United States Patent [19]

Niederer et al.

[11] Patent Number: 4,698,359

[45] Date of Patent: Oct. 6, 1987

[54] MEDICATED SUPPOSITORY

[75] Inventors: Roland R. Niederer, Stetten; Hans W. Zulliger, Andelfingen, both of Switzerland

[73] Assignee: Cilag, AG, Schaffhausen, Switzerland

[21] Appl. No.: 739,808

[22] Filed: May 31, 1985

Related U.S. Application Data

[63] Continuation-in-part of Ser. No. 411,123, Aug. 24, 1982, abandoned.

[51] Int. Cl.$^4$ ............................................ A61K 31/415
[52] U.S. Cl. .................................... 514/396; 514/966; 514/967; 424/DIG. 15

[58] Field of Search ....................... 514/396, 966, 967; 424/DIG. 15

[56] References Cited

U.S. PATENT DOCUMENTS 4,291,062  9/1981  Leigh et al. ..................... 514/5.88
4,347,237  8/1982  Evenstad et al. ..................... 424/78

Primary Examiner—Johnnie R. Brown
Assistant Examiner—John W. Rollins
Attorney, Agent, or Firm—Benjamin F. Lambert

[57] ABSTRACT

A medicated suppository for use in the vaginal or rectal cavity comprising a medicament, a mixture of triglycerides of fatty acids, a gel forming agent and a gel dispersing agent is described.

9 Claims, No Drawings

MEDICATED SUPPOSITORY

This is a continuation-in-part of application Ser. No. 411,123, filed Aug. 24, 1982, now abandoned.

This invention relates to a medicated suppository for vaginal or rectal application. In particular the invention relates to a medicated suppository which is capable of releasing the medicament evenly over the walls of the vaginal or rectal cavity. The invention consists of a triglyceride based suppository and is comprised of a medicament, a gel forming agent and a gel dispersing agent.

The administration of medicaments in the form of suppositories is known in the art. In general usage, however, it has been found that upon liquefaction of the suppository some of the fluid containing the medicament flows out of the vaginal or rectal cavity leaving less of the medicament available for the intended therapeutic use. To counteract this loss of medicament, suppositories containing higher concentrations of the medicament are sometimes employed. However, as a result of the higher concentration of medicament, the patient is exposed to higher doses of the drug than are actually required for successful treatment. In addition, the cost of the therapy is of necessity higher due to the use of excess medicament. There is a need, therefor, for a suppository which will melt quickly in body fluids but will maintain contact between the area to be treated and the medicament for extended periods of time.

The suppository of the present invention is comprised of a triglyceride, as the carrier, a gel forming agent and a gel dispersing agent in combination with a medicament. The desired therapeutic effect is achieved by diffusion of the medicament throughout the vaginal or rectal cavity by the action of the dispersing agent and the adhesive properties of the gel forming agent which combine to prevent the liquified suppository from flowing out of the vaginal or rectal cavity. The availability of the medicament is thus increased by the resultant increase in the adhesion properties of the mixture and the extension of the time during which the medicament resides in the vaginal or rectal cavity. The unique combination of ingredients results in a homogeneous composition which is capable of distributing the medicament throughout the vaginal or rectal cavity. This results in the administration of smaller doses of the medicament than those required in conventional suppositories.

According to the present invention, a triglyceride is employed as the carrier in the suppository. The triglyceride carrier is present in a ratio of about 60%–87% by weight. Mixtures of mono-, di- and triglycerides of the fatty acids $C_{10}H_{20}O_2$ to $C_{18}H_{36}O_2$ (hard fat commonly known in the art as Adeps solidus) may be employed. The materials are sold under the tradenames Witepsol H19, Wecobee, Novata 299, Witepsol H12 and Witepsol S55 and are synthetic triglyceride mixtures which are produced from a variety of vegetable oils, such as coconut and palm kernel oils, by esterification, hydrogenation and fractionation to obtain products of varying composition. The fatty acid moiety of the ester varies in carbon chain length from $C_{10}$ to $C_{18}$ and contains a high percentage of lauric acid ($C_{12}$).

The chemical and physical properties of the hard fats are defined by controlling the percentage of a particular fatty acid fraction in the molecule and the amount of monoglycerides and diglycerides. The compositions are generally characterized by melting range and hydroxyl value (i.e. mono-, diglyceride content). For example, Witepsol H19 has a hydroxyl value between 20–30 and a melting range of 33.5°–35.5° C., Wecobee FS has a maximum hydroxyl value of 10 and a melting range of 38°–42° C., Novata 299 has a maximum hydroxyl value of 5.0 and a melting range of 33.5°–35.5° C., Witepsol H12 has a maximum hydroxyl value of 15.0 and a melting range of 32°–33.5° C., and Witepsol S55 has a hydroxyl value between 50–65 and a melting range of 33.5°–35.5° C. The properties of the hard fats (adeps solidus) vary according to percentage of lauric acid present and the amount of the tri- di- and monoglycerides present.

As the gel forming agent materials such as polygum, (a gel forming agent containing guar gum), guar gum, alkali metal and alkaline earth metal salts of alginic acid, polygel (a hydrocolloidal polysaccharide consisting of ⅔ galactomannan and ⅓ xanthan gum) and xanthan gum may by employed. The gel forming agent is present in a ratio of about 5–25% by weight.

As the gel dispersing agent materials such as stearyl heptanoate, purcelline oil (cetearyl octanoate), partial fatty acid glycerol esters and surface active agents such as polyethylene sorbitan fatty acid esters (Tween) may be employed. The gel dispersing agent is present in a ratio of about 4–8% by weight.

The invention is comprised of a suppository having two phases: a "fatty phase" and a "jelly phase." The carrier, gel dispersing agent and surfactant together comprise a fast melting suppository. In the first phase the mixture melts upon contact with the body cavity and the resulting mixture spreads over the vaginal or rectal epithelium. In the second phase the gel forming agent present in the melt transforms the melt into a jelly-like consistency on the surface of the vaginal or rectal epithelium. Normally, the vaginal moisture viscosity at this point will be high. The jellying effect leads to in situ formation of a jelly-like carrier-matrix for the active ingredient. The medicament is then gradually released from the carrier-matrix on the walls of the vaginal epithelium. The availability of the medicament is thus enhanced by the resultant increase in the surface of adsorption and the extension of the time during which the medicament resides in the vaginal or rectal cavity.

The formulation may be employed with one or more of a number of known medicaments including antibiotics such as tetracycline hydrochloride, erythromycin, neosporin, achromycin and chloromycetin, for example; antimycotics such as econazole nitrate, miconazole nitrate, terconazole and clotrimazole, for example; anti-inflammatory agents such as aspirin, clocortolone pivalate, hydrocortisone, tolmetin sodium and indomethacin, for example; estrogens, anthelmintics; anti-inflammatory agents and disinfectants such as benzalkonium for example. The amount of medicament present in the suppository will depend upon the particular medicament employed, however, ratios of about 4–15% by weight of a given medicament may be employed.

In certain formulations better homogenicity may be obtained by the use of a stabilizer for the colloidal suspension. Colloidal silicon dioxide or urea can be used as the stabilizing agent. In those cases where the medicament is only moderately soluble in the suppository formulation, a solubilizing agent such as sorbitan monostearate or polyethylene glycol may be employed. With certain medicaments, it may be necessary to employ a preservative such as benzoic acid, for example, or an anti-oxidant such as butylated hydroxytoluene, for example, in the formulation. In some instances more than one medicament may be employed in a given suppository.

The suppository of the present invention is generally prepared by first mixing the gel forming agent and the medicament in a suitable vessel and micronizing the mixture. The medicament is then added in portions; after each addition the granules are pressed through a sieve and the mixing is continued for several minutes. In a separate vessel the fatty acid triglyceride and the gel dispersing agent are melted together at a temperature of about 50°-60° C. The melt is cooled to about 40° C. The two mixtures are combined with stirring and the combined mixture is then homogenized for about 10 minutes at a temperature between 38°-40° C. The mixture is then cooled to about 36°-39° C. and placed in a suppository shell. If a stabilizing agent is to be employed in the suppository, it is generally added to the mixture of the fatty acid triglyceride and the gel dispersing agent after the melt has been cooled. However, the solubilizing agents and preservatives, when employed, can be added at various stages during the procedure.

Although the suppository of the present invention may be prepared in a variety of shapes, the preferred shape is an egg-shaped ovule. The suppository has a weight between about 1 and 3 g. The preferred weight is between about 2.2-2.7 g.

A more detailed description of the process according to the invention is described in Procedure 1.

PROCEDURE 1

A. Polygel (24 Kg) is placed in a mixing vessel. Econazole nitrate (8 Kg) is added in portions and the mixture is micronized and mixed for 5 minutes. After each addition of econazole nitrate, the granules are pressed through an 0.4 mm sieve and then mixed for 10 minutes.

B. In a separate vessel adeps solidus (Witepsol H 19; 64.72 Kg), adeps solidus (Wecobee FS; 269.18 Kg) and stearyl heptanoate (21.82 Kg) are added together and the mixture is melted at 50°-60° C. The melt is cooled to 40° C. colloidal silicon dioxide (4.32 Kg) is added and the mixture is homogenized for 5 minutes. This mixture is then combined with the mixture prepared in A above with stirring and the resulting mixture is homogenized for 10 minutes at 38°-40° C. under vacuum. The homogenate is then cooled to 36°-39° C. in vacuo and placed in a multiplast container.

The following are examples of suppositories falling within the present invention.

|  | mg/suppository |
|---|---|
| Example 1 | |
| Econazole nitrate | 150.0 |
| Polygel | 300.0 |
| Colloidal silicon dioxide | 27.0 |
| Adeps solidus (Witepsol H 19) | 404.2 |
| Adeps solidus (Wecobee FS) | 1682.4 |
| Stearyl heptanoate | 136.4 |
| Example 2 | |
| Metronidazole | 350.0 |
| Alginate | 350.0 |
| Colloidal silicon dioxide | 27.0 |
| Adeps solidus (Novata 299) | 413.0 |
| Adeps solidus (Wecobee FS) | 1410.0 |
| Softigen 701 (glyceryl hydroxystearate) | 150.0 |
| Example 3 | |
| Estriol | 0.5 |
| Benzoic acid | 0.8 |

-continued

|  | mg/suppository |
|---|---|
| Butylated Hydroxytoluene | 0.5 |
| Polygel | 300.0 |
| Polyethylene glycol 400 | 60.0 |
| Polyethylene glycol 1000 | 300.0 |
| Sorbitan monostearate (Span 60) | 215.0 |
| Adeps solidus (Witepsol S 55) | 1823.2 |
| Example 4 | |
| Sulfathiazole | 170.0 |
| Sulfacetamide | 145.0 |
| Sulfabenzamide | 180.0 |
| Urea | 32.0 |
| Polygel | 300.0 |
| Adeps solidus (Witepsol H 12) | 1873.0 |
| Example 5 | |
| Chlorquinaldol | 200.0 |
| Oxychinolin sulfate | 10.0 |
| Polygum | 350.0 |
| Colloidal silicon dioxide | 25.8 |
| Adeps solidus (Witepsol H 19) | 429.7 |
| Adeps solidus (Wecobee FS) | 1547.0 |
| Stearyl heptanoate | 137.5 |

The suppositories prepared according to the above examples liquefy in body fluids in less than thirty minutes at about 37° C.

The above examples are provided by way of illustration and are not meant to limit the scope of the present invention, the scope of which is defined by the appended claims.

What is claimed is:

1. A medicated suppository comprising about 60–87% by weight of a mixture of triglycerides of the fatty acids $C_{10}H_{20}O_2$ to $C_{18}H_{36}O_2$; 5–25% by weight of a gel forming agent selected from the group consisting of polygum, guar gum, alkali metal and alkaline earth metal salts of alginic aid, polygel and xanthan gum; 4–5% by weight of a gel dispersing agent selected from the group consisting of stearyl heptanoate, purcelline oil, partial fatty acid glycerol esters and polyethylene sorbitan fatty acid esters and 4–15% by weight of a medicament.

2. The medicated suppository of claim 1 wherein the medicament is selected from econazole nitrate, miconazole nitrate, terconazole and clotrimazole.

3. The medicated suppository of claim 1 wherein a stabilizer is additionally present.

4. The medicated suppository of claim 3 wherein the stabilizer is silicon dioxide.

5. The medicated suppository of claim 1 or 4 which comprises 5.56% by weight of econazole nitrate, 11.11% by weight of polygel, 1.0% by weight of colloidal silicon dioxide, 14.97% by weight of a hard fat having an hydroxyl value of 20–30 and a melting range of 33.5°–35.5° C., 62.31% by weight of a hard fat having a maximum hydroxyl value of 10 and a melting range of 38°–42° C. and 5.05% by weight of stearyl heptanoate.

6. The suppository of claim 1 wherein the weight of the suppository is between 1 and 3 g.

7. A suppository base comprising 60–87% by weight of a mixture of triglycerides of the fatty acids $C_{10}H_{20}O_2$ to $C_{18}H_{36}O_2$; 5–25% by weight of a gel forming agent selected from the group consisting of polygum, guar gum, alkali metal and alkaline earth metal salts of alginic acid, polygel, and xanthan gum and 4–8% by weight of a gel dispersing agent selected from the group consisting of stearyl heptanoate, purcelline oil, partial fatty acid glycerol esters and polyethylene sorbitan fatty acid esters.

8. The suppository base of claim 7 wherein a stabilizer is additionally present.

9. The suppository base of claim 8 wherein the stabilizer is silicon dioxide.

* * * * *